United States Patent [19]

Uchino et al.

[11] Patent Number: 4,751,686
[45] Date of Patent: Jun. 14, 1988

[54] ULTRASONIC MICROSCOPE

[75] Inventors: Fumio Uchino; Kouji Taguchi, both of Hachioji, Japan

[73] Assignee: Olympus Optical Co., Ltd., Tokyo, Japan

[21] Appl. No.: 861,910

[22] Filed: May 12, 1986

[30] Foreign Application Priority Data

May 14, 1985 [JP] Japan .................................. 60-102039
May 14, 1985 [JP] Japan ............................. 60-71092[U]
Sep. 3, 1985 [JP] Japan ............................ 60-133990[U]

[51] Int. Cl.[4] ....................... G03B 42/06; G01N 9/24; G01N 29/00; G01N 29/04
[52] U.S. Cl. ......................................... 367/7; 73/606; 73/609; 73/614; 73/615
[58] Field of Search ....................... 367/7, 87, 99, 191; 73/606, 609, 610, 614, 615

[56] References Cited

U.S. PATENT DOCUMENTS

| 4,012,951 | 3/1977 | Kessler | 367/7 |
| 4,174,634 | 11/1979 | Dory | 73/606 |
| 4,174,635 | 11/1979 | Oldendorf | 73/606 |
| 4,212,206 | 7/1980 | Hartemann et al. | 73/606 |
| 4,241,608 | 12/1980 | Dees et al. | 73/606 |
| 4,463,608 | 8/1984 | Takeuchi et al. | 73/606 |
| 4,484,476 | 11/1984 | Nagasaki | 73/606 |
| 4,577,504 | 3/1986 | Kanda et al. | 73/606 |

FOREIGN PATENT DOCUMENTS

| 0084174 | 7/1983 | European Pat. Off. |
| 2846655 | 5/1979 | Fed. Rep. of Germany |
| 2941861 | 6/1981 | Fed. Rep. of Germany |
| 3415283 | 10/1984 | Fed. Rep. of Germany |

Primary Examiner—Stephen C. Buczinski
Assistant Examiner—Melissa Koltak
Attorney, Agent, or Firm—Armstrong, Nikaido, Marmelstein & Kubovcik

[57] ABSTRACT

In order to replace acoustic lenses, frequency units corresponding to frequencies used by the acoustic lenses and housing transmitted pulse generating means, circulators and receiving means can be selected and the signal of a gate opening at a timing at which ultrasonic waves of a sample return can be selected.

7 Claims, 8 Drawing Sheets

ULTRASONIC MICROSCOPE

FIELD OF THE INVENTION AND RELATED ART STATEMENT

This invention relates to an ultrasonic microscope wherein an acoustic observed image by ultrasonic waves can be obtained by replacing an acoustic lens.

As different from an optical microscope and an electronic microscope by utilizing electronic rays, an ultrasonic microscope whereby an acoustic picture image information can be obtained has recently come to be noted.

With the above mentioned ultrasonic microscope, an ultrasonic microscope picture image having a resolving power in the order of μm can be obtained by using ultrasonic waves, for example, of 100 MHz to several GHz.

In such ultrasonic microscope, in principle, a sample plane is mechanically scanned with a finely throttled ultrahigh frequency ultrasonic wave beam, the ultrasonic waves dispersed by the sample are converged and converted to an electric signal and this signal is two-dimensionally displayed on such displaying picture surface as of a cathode-ray tube to obtain a microscope image. The formation is divided depending on the manner of detecting ultrasonic waves into a passing type detecting ultrasonic waves coming to pass while being dispersed and attenuated within the sample and a reflecting type detecting ultrasonic waves coming to be reflected by the difference of the acoustic properties within the sample.

Figure 1:
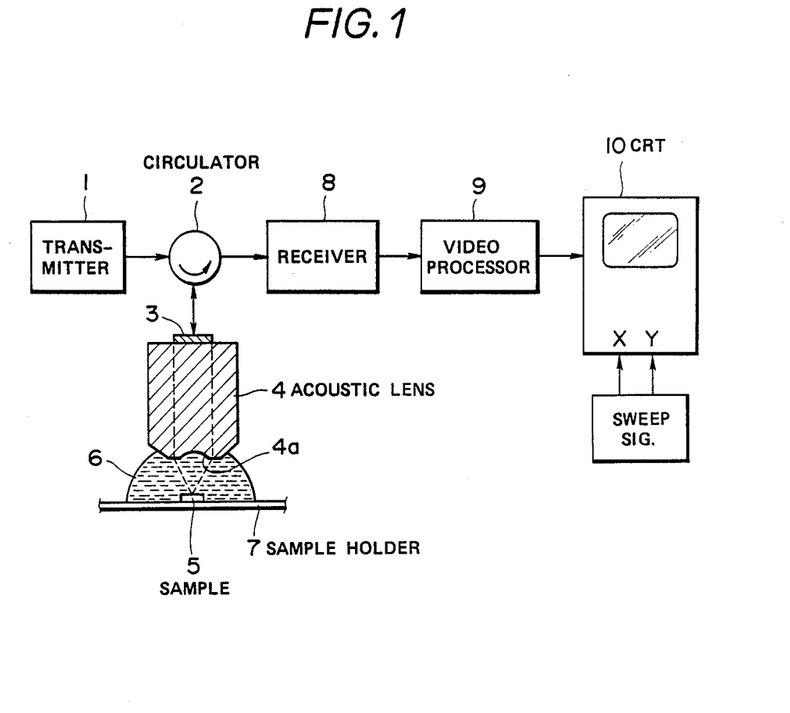
FIG. 1 is a principle view of an ultrasonic microscope.

FIG. 1 is a principle view of a reflecting type ultrasonic microscope wherein a signal from a transmitter 1 is fed to a transmitting and receiving piezoelectric transducer 3 by a directive connector or circulator. This signal is converted to an ultrasonic wave and this wave is radiated in the form of a plane wave through one surface into an ultrasonic wave converging lens (acoustic lens) 4 which is made of such ultrasonic wave propagating medium as a sapphire and to whose one surface (upper end surface) this piezoelectric transducer 3 is pasted, is sent to the other surface side of this acoustic lens 4 spherically incised to form a spherical lens part 4a, is propagated in the form of a spherical wave through such ultrasonic wave propagating medium 6 as water interposed between this spherical lens part 4a and a sample 5 opposed to it and is converged in the form of a beam spot on the surface of the sample 5 (in case the acoustic lens 4 is focused on the surface).

The above mentioned sample 5 is arranged on a sample holder 7. The ultrasonic wave transmitted to this sample 5 side is passed or absorbed in response to the acoustic characteristics on the sample surface, a part of the reflected wave and dispersed wave passes through the same course, is converted to an electric signal by the piezoelectric transducer 3 and is put into the receiver 8. The signal is detected by this receiver 8 and its output is put into such displayer 10 as a CRT through a video signal processor 9. On the other hand, the above mentioned acoustic lens 4 is scanned, for example, in the X-direction by a vibrator not illustrated, the sample holder 7 side is scanned in the Y-direction, a sweep signal synchronized with these scans is impressed on the X and Y-axes and a two-dimensional ultrasonic microscopic picture image is displayed on the displaying picture surface of this displayer 9.

Now, the above mentioned ultrasonic microscope has a feature that, if the focus position in the Z-axis direction vertical to the X and Y-planes is varied, that is to say, if the acoustic lens 4 is brought closer to the sample side and is focused within the sample, an ultrasonic microscopic picture image will be able to be obtained.

However, the higher the frequency of a transmitter to be applied, the more quickly the attenuation amount per unit distance of the ultrasonic wave propagating medium 6 increases for obtaining a higher resolution image. Therefore, in the case of observing the interior region of the sample, it is necessary to compromise the frequency to be applied.

It is also necessary to consider the opening angle of an acoustic lens by the reason of the physical property of a sample causing the opening angle to be wider for allowing the known reflected wave to be received by the lens.

Another consideration to determine an acoustic lens structure is the operating distance between the spherical lens part and a sample because it reflects the gating timing of the reflected signal.

A known theory to determine the length of an acoustic lens L describes a frequent dependency. Therefore, to provide for various needs of an acoustic microscope, it is found that plural types of acoustic lenses with specific frequencies are designed and they are replaced for respective purposes in the mounting position of an ultrasonic microscope and sometimes to change an adjusting unit for respective lenses such as a matching box for matching the impedance of the particular frequency to be used.

Now, in case the frequency is changed, it will be necessary to replace a matching box together with a transmitter 1, circulator 2, receiver 8 and acoustic lens 4.

Figure 2:
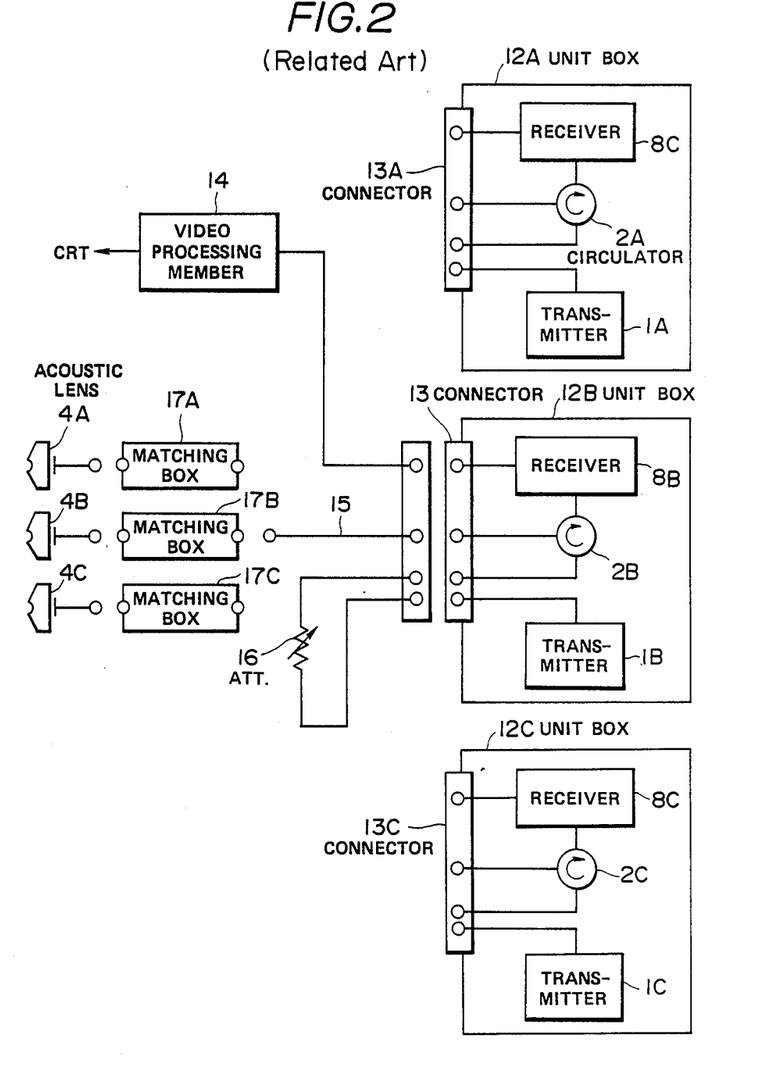
FIG. 2 is a formation view showing a frequency changing device in a prior art example.

Therefore, in a prior art, as shown in FIG. 2, a video signal processing portion 14, cable 15 and attenuator 16 can be connected by respective connectors 13A, 13B and 13C provided respectively on (frequency) unit boxes 12A, 12B and 12C respectively containing and connecting transmitters 1A, 1B and 1C, circulators 2A, 2B and 2C and receivers 8A, 8B and 8C for respective frequencies. The above mentioned cable 15 can be connected at one end to the circulators 2A, 2B and 2C and at the other end to matching boxes 17A, 17B and 17C which are connected respectively to acoustic lenses 4A, 4B and 4C.

Therefore, this prior art example requires operations of replacing the unit boxes 12A, 12B and 12C, replacing the matching boxes 17A, 17B and 17C and replacing the acoustic lenses 4A, 4B and 4C. Thus, there is a defect that many operations are required for the observation at such different frequencies as of the above mentioned unit boxes 12A, 12B and 12C. There is also a disadvantageous problem that, in fitting, the electric connection of the connector parts will not be always positive.

In the case of replacing the acoustic lens 4, depending on the acoustic lens to be used, the time until the reflected wave reflected by the sample 5 returns to the receiver will be different and therefore the timing of generating the gate signal for taking in the reflected wave will have to be set at a proper value. In the prior art example, there is a defect that, whenever the acoustic lens 4 is replaced, the timing will have to be set in an optimum state.

OBJECTS AND SUMMARY OF THE INVENTION

An object of the present invention is to provide an ultrasonic microscope wherein an observation at different frequencies can be made by a simple operation.

Another object of the present invention is to provide an ultrasonic microscope wherein an observation can be made under optimum conditions within a short time.

Further another object of the present invention is to provide an ultrasonic microscope wherein troubles are few and the reliability can be improved.

The ultrasonic microscope of the present invention comprises a means of selecting a plurality of frequency unit boxes containing respectively transmitted pulse generating means, circulators and receiving means provided in response to acoustic lenses to be used and a means of selecting and setting a timing of putting out a gate signal making it possible to take in a reflected ultrasonic wave returning from the sample side in response to the lens length of the acoustic lens.

DETAILED DESCRIPTION OF PREFERRED EMBODIMENTS OF THE INVENTION

Figure 3:
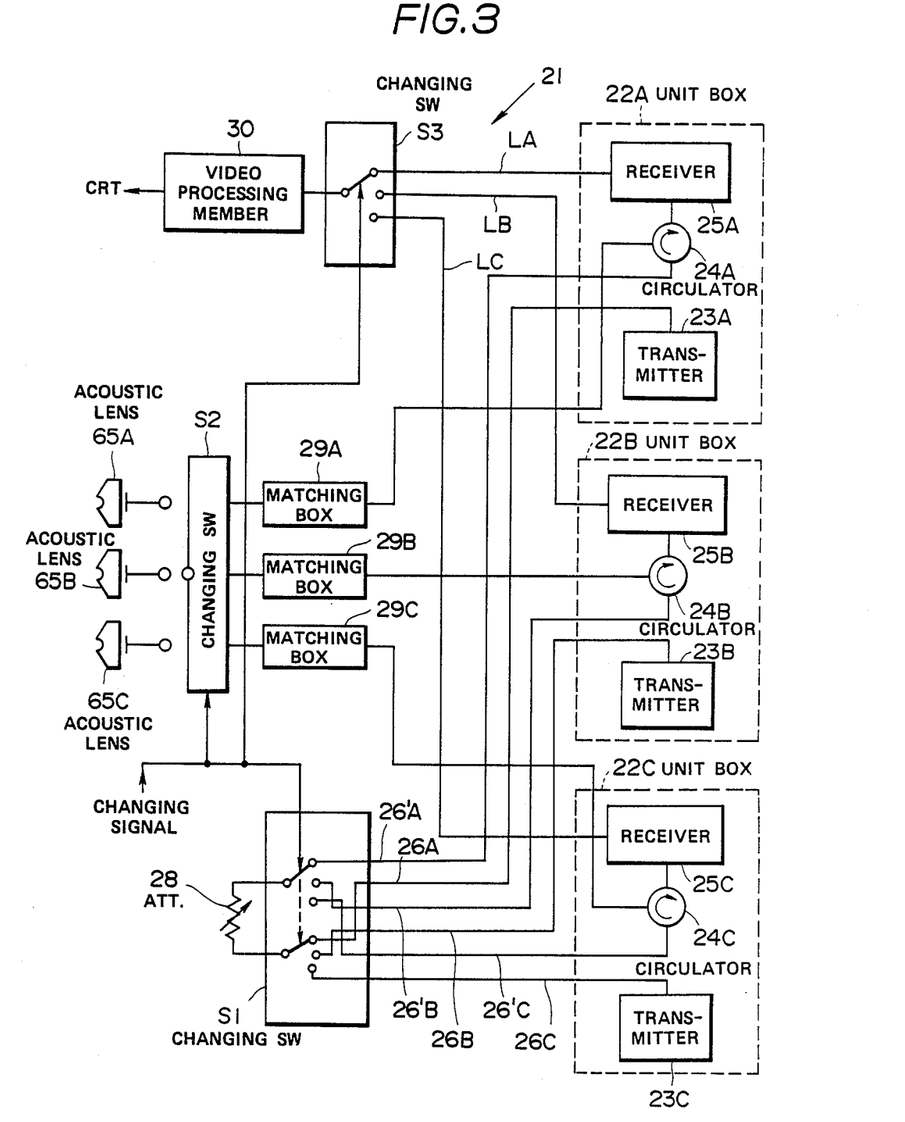
FIG. 3 is a formation view showing a frequency changing device in the first embodiment of the present invention.

As shown in FIG. 3, a changing means 21 in the first embodiment contains respectively transmitters 23A, 23B and 23C, circulators 24A, 24B and 24C and receivers 25A, 25B and 25C, for example, in three respective unit boxes 22A, 22B and 22C.

The output line 26I of the transmitter 23I within the above mentioned same unit box 22I (I=A, B or C) and the (transmitting input) line 26'I of the circulator 24I to be connected to this output line can be connected to the respective terminals of an attenuator 28 which can vary the attenuation amount through a first change switch or changing switch S1.

The above mentioned first change switch S1 is formed, for example, of a coaxial relay switch so that a combination in which the attenuator 28 is interposed and connected between the transmitter 23I and circulator 24I may be alternatively selected by a change signal. By the way, the change signal is so made that a corresponding change signal may be put out, for example, by the operation of three frequency selecting buttons provided on the operating panel or the like of an ultrasonic microscope not illustrated and that the attenuator 28 may be connected to the unit box 22I of the corresponding frequency by this change signal.

The lines conducted at the time of transmitting and receiving signals in the circulators 24I of the respective unit boxes 22I are connected to the matching boxes 29I containing matching means for matching at the respective frequencies. This matching box 29I can be conducted to the acoustic lens 65I fixed to the lens fitting part through a second change switch S2 which is made also, for example, of a coaxial relay switch or the like so that one of the three matching boxes 29A, 29B and 29C may be selectively conducted by the above mentioned change signal.

Further, the respective output lines LA, LB and LC of the receivers 25I are connected to a video signal processing member 30 through a third change switch S3 and the outputs of the receivers 25I are made an image signal output in this video signal processing member 30 and are displayed in such displayer as a CRT.

With the above mentioned third change switch S3, one of the three output lines LA, LB and LC can be also selectively connected with the video signal processing member 30 by the above described change signal.

According to the first embodiment provided with the thus formed changing device, in the case of the observation with any one of the three frequencies, if the acoustic lens (for example, 65B) corresponding to the frequency to be used is merely fitted to the lens fitting part and a frequency selecting button provided on the operating panel or the like is operated, by this operation, the first change switch S1 will interpose and connect the attenuator 28 between the transmitter 23B and circulator 24B of the unit box 23B of the same frequency as of the above mentioned acoustic lens 65B, the second change switch S2 will connect the matching box 29B and acoustic lens 65B with each other and the third change switch S3 will connect the output line LB of the receiver 25B with the video signal processing member 30.

Therefore, there are advantages that, with a very simple operation, the frequency can be changed in the observation and also that, according to this first embodiment, the frequency can be changed within a short time in observing even a sample whose acoustic characteristics are changeable with the time. Further, the electric connection can be set to be more positive and reproducible than in the case of mechanically removably using the connector. Therefore, such trouble as a faulty connection can be reduced and the reliability of the device can be improved.

By the way, in the above mentioned first embodiment is explained the changing device 21 which can be utilized with three different frequencies. However, the present invention is not limited to this and can be applied to the case with two frequencies or the case with four or more frequencies. The means set to be electrically changed can be replaced.

By the way, in the above mentioned first embodiment, only the acoustic lenses 65A, 65B and 65C are replaceably fitted and the other parts are electrically connected as required by the change switches S1, S2 and S3. However, the modifications of such combination belong to the present invention.

Also, a plurality of acoustic lenses may be fitted, moved and rotated and one of them may be selectively set to be used by operating such electric driving means as a solenoid or motor with an electric switch or the like.

Figure 4:
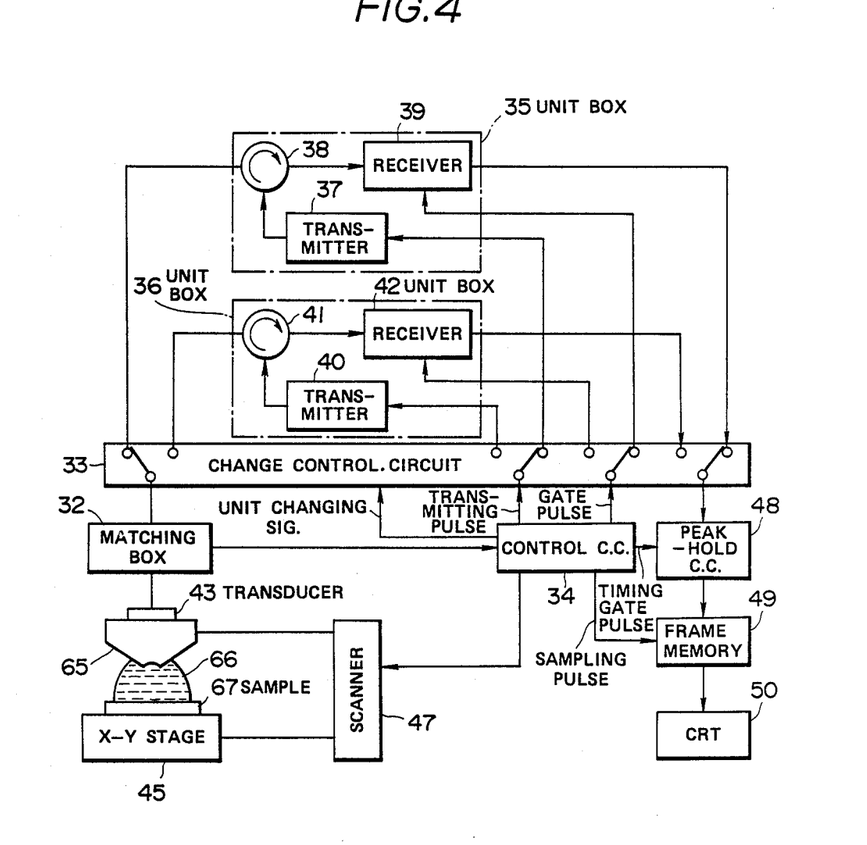
FIG. 4 is a formation view showing a frequency changing means in the second embodiment of the present invention.

FIG. 4 shows the second embodiment of the present invention wherein two acoustic lenses can be selectively fitted. An acoustic lens 65 and a matching means 32 corresponding to it are removably fitted respectively in predetermined positions in an ultrasonic microscope so as to connect the acoustic lens 65 and matching means 32 with each other and to connect the matching means 32 to a change controlling circuit 33. The matching means 32 has a discriminating signal generating means generating a lens discriminating signal for the corresponding acoustic lens 65. The lens discriminating signal is fed to a control circuit 34 by fitting the matching means 32 in a predetermined position in the ultrasonic microscope and is read in the control circuit 34.

Two frequency units 35 and 36 contained in response respectively to two replaceable acoustic lenses are connected to the change controlling circuit 33. One of these frequency units 35 and 36 is selected by a unit changing signal produced on the basis of the lens discriminating signal read in the control circuit 34.

The frequency unit 35 is provided with a transmitter 37, circulator 38 and receiver 39 and, in the same manner, the frequency unit 36 is provided with a transmitter 40, circulator 41 and receiver 42 so that the frequency unit corresponding to the acoustic lens 65 may be selected through the change controlling circuit 33. In FIG. 4, a transmitted pulse signal corresponding to the acoustic lens 31 is fed in the same manner from the control circuit 34 to the transmitter 37 of the frequency unit 35 to generate a burst wave signal which is fed to a piezoelectric transducer 43 fitted to the acoustic lens 31 through the change controlling circuit 33 and matching means 32, is converted here to an ultrasonic wave and is projected as a spot onto a sample 46 through the acoustic lens 31 and water 44 as an ultrasonic wave transmitting medium. By the way, the acoustic lens 31 is vibrated at a high speed in the X-direction by a scanning mechanism 47 under the control of the control circuit 34 and an X-Y stage 45 is moved in the Y-direction by the scanning mechanism 47 to two-dimensionally scan the sample 46.

The reflected wave of the ultrasonic wave projected onto the sample 46 is converged by the acoustic lens 31 through water 44 and is converted to an electric signal by the piezoelectric transducer 43 and the electric signal is then fed to the receiver 39 through the matching means 32, change controlling circuit 33 and circulator 38 of the frequency unit 35 corresponding to the selected acoustic lens 31 and here only the signal corresponding to the reflected wave of the sample 46 is taken out by the gate pulse signal corresponding to the acoustic lens 31 fed from the control circuit 34 through the change controlling circuit 33 and is fed to a peak holding circuit 48 through the change controlling circuit 33. In the peak holding circuit 48, the peak of the output of the receiver 39 is held by the sampling gate pulse signal for holding the peak corresponding to the acoustic lens 65 fed from the control circuit 34, is housed in a picture image memory 49 by the sampling pulse signal corresponding to the acoustic lens 65 fed from the control circuit 34 and is displayed in a CRT 50.

That is to say, in this embodiment, the frequency, lens length, operating distance and opening angle of the fitted acoustic lens 65 are read from the lens discriminating signal from the matching means 32 in the control circuit 34, thereby a unit changing signal is put out in the change controlling circuit 33, the corresponding frequency unit 35 is automatically selected and each of the transmitting pulse signal, gate pulse signal, sampling gate pulse signal and sampling pulse signal is automatically set at a proper value of the fitted acoustic lens 65.

By the way, in this embodiment, two acoustic lenses are made replaceable. However, even in case more acoustic lenses are made replaceable, the same formation will be able to be used. In FIG. 4, the reference numeral 66 represents water and 67 represents a sample.

Figure 5A:
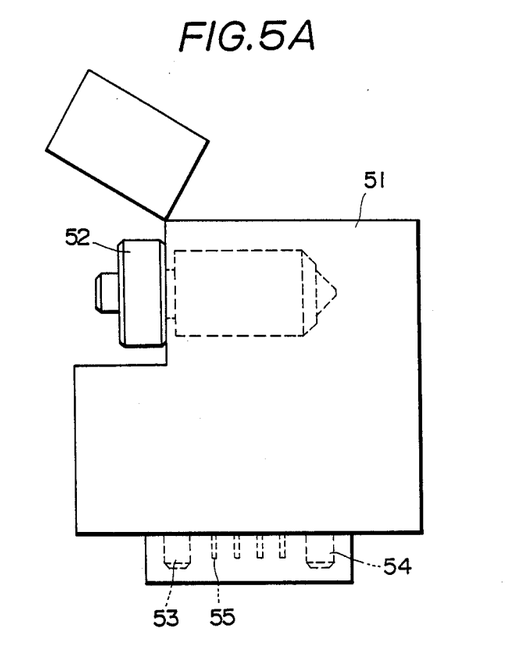
FIG. 5A is a plan view showing an acoustic lens and an embodiment of a matching means fitted with this acoustic lens.
Figure 5B:
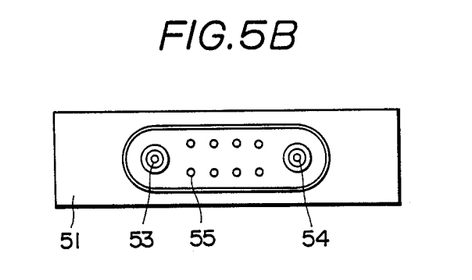
FIG. 5B is an elevation of FIG. 5A.

FIGS. 5A and 5B are respectively a plan view and elevation showing a formation of an example of the matching means used in this embodiment. As described above, as the acoustic lens and matching means correspond to each other, in this embodiment, the acoustic lens 52 corresponding to the matching means 51 can be removably contained. The fitting part of the matching means 51 to the ultrasonic microscope is provided with a terminal 53 for connecting to the acoustic lens 52 and a terminal 54 connected to the circulator 38 or 41 of the frequency unit 35 or 36 through the change controlling circuit 33 as explained in FIG. 4 and with, for example, 8 connecting pins 55 for generating a lens discriminating signal so that, by these 8 connecting pins 55, the lens discriminating signal may be fed as information of 8 bits to the control circuit 34 (See FIG. 4).

According to this embodiment, by fitting the matching means corresponding to the acoustic lens, the electric circuit can be automatically variously set with the exchange of the acoustic lens and therefore the exchanging operation is easy and can be positively made without causing errors.

Now, the third embodiment wherein the gate pulse signal automatically selected on the basis of the above mentioned discriminating signal is changed shall be explained in the following. By the way, this embodiment is to set the gate pulse signal to be optimum in response to the acoustic lens to be used and need not always be of different frequencies.

Figure 6:
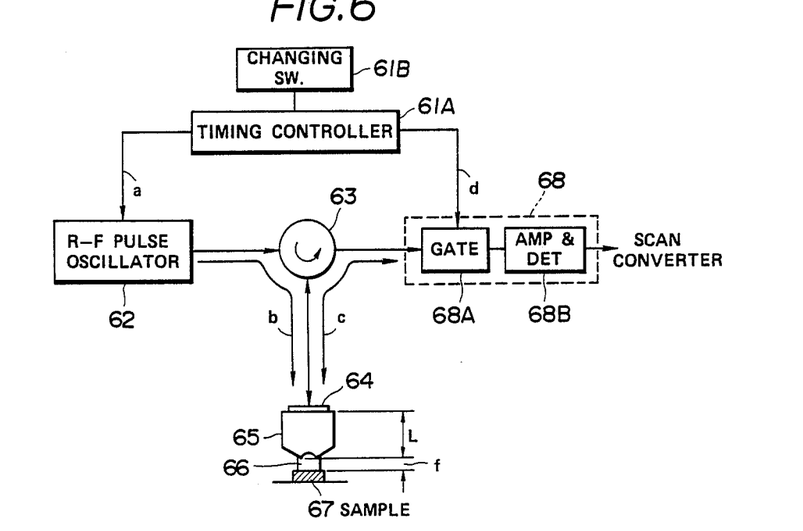
FIG. 6 is a block diagram of an essential part of a gate timing changing device in the third embodiment of the present invention.

FIG. 6 is of a circuit wherein a control signal a is output to a high frequency pulse generating part 62 by a timing controller 61A and a gate signal d of an optimum timing corresponding to each of a plurality of acoustic lenses 65 of different designs is selected by the selecting operation of the change switch 61B and is output to the gate part 68A of a receiver 68. The timing controlling part 61A is formed within the control circuit 34 shown in FIG. 4. A high frequency burst signal b is output of the high frequency pulse generating part 62 by the control signal a, is added to a piezoelectric transducer 64 reversibly converting an electric signal and ultrasonic signal through a circulator 63 and is converted to an ultrasonic wave. This ultrasonic wave is converged by an acoustic lens 65 and is projected as a minute spot onto a plane of a sample 67 through such ultrasonic wave transmitting medium 66 as, for example, water. The piezoelectric transducer 64 and acoustic lens 64 are made integral to form an ultrasonic head and are made replaceable. The projected ultrasonic wave reflects in response to the acoustic characteristics of the sample 67, is converged by the acoustic lens 65, is received by the piezoelectric transducer 64, is converted to an electric signal c and is led to the receiver 68 again through the circulator 63. The above mentioned electric signal c led to this receiver 68 is gated by a gate signal d of an optimum timing from the timing controller 61A in a gate 68A of the receiver 68, the unnecessary signal (reflected wave from within the acoustic lens 65)

is removed and only the required signal (reflected wave from the sample 67) is amplified and detected by the amplifying and detecting part 68B of the receiver 68 and becomes a detected output signal corresponding to the reflecting intensity from the sample 67. This detected output signal is led to a scan converter not illustrated. By the way, the sample 67 is placed on a sample stand scanned and controlled in the X-direction and Y-direction.

Figure 7:
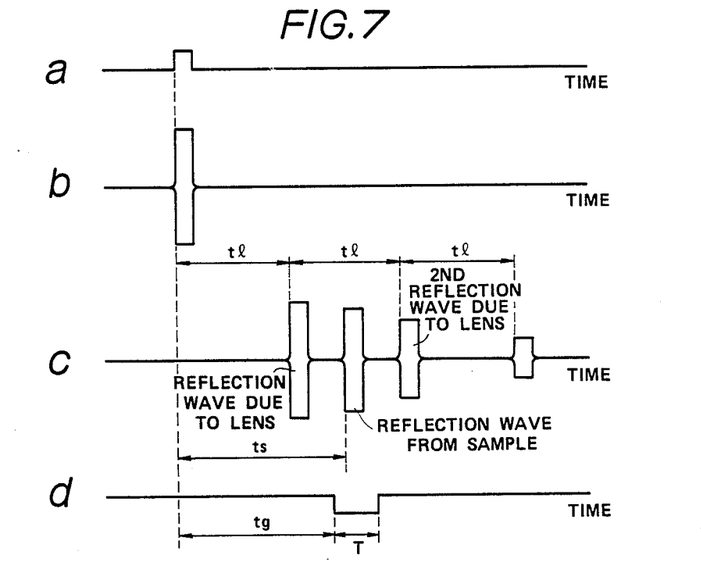
FIGS. 7 to 9 are waveform views showing timings of signals in the respective parts in FIG. 6 in case three acoustic lenses are replaced and used.
Figure 8:
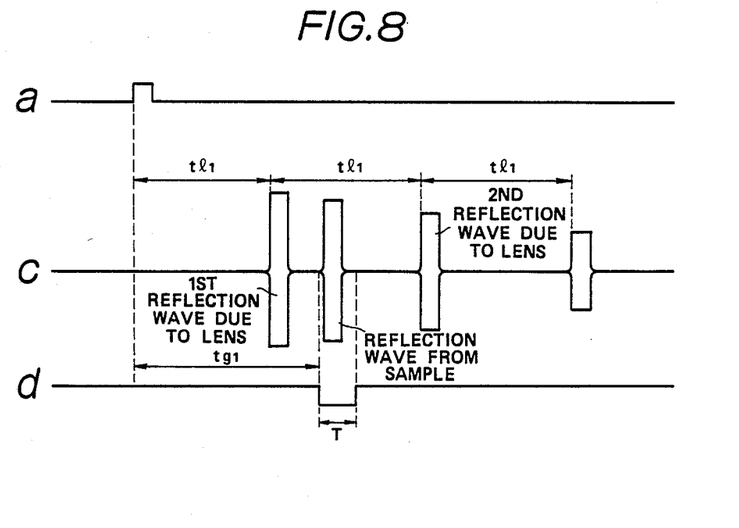
Figure 9:
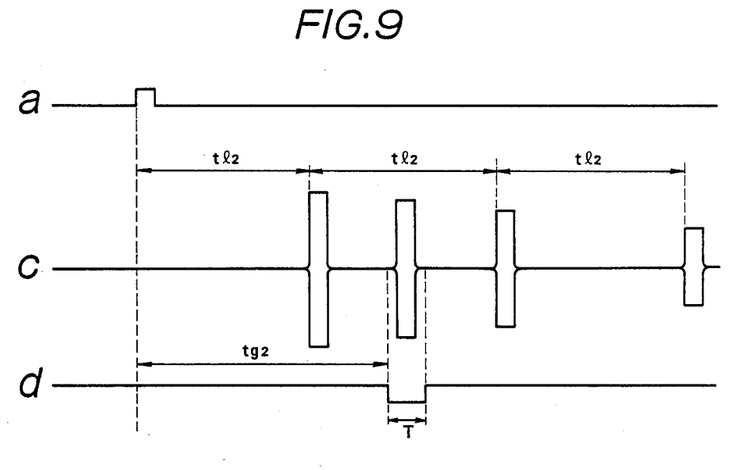

In the microscope device formed as in the above, in case an acoustic lens of a length L and a focal distance f by the curvature is used for the acoustic lens 65 and is focused on the surface of the sample 67, the timings of the signals a, b, c and d will be as shown in FIG. 7. In FIG. 8, a represents a control signal put out to the high frequency pulse generating part 62 from the timing controller 61A. On the basis of this control signal a, in the timing controller 61A, the gate signal d of a predetermined time width T delayed by a time tg from the signal a and reversed is made and put out. This gate timing tg is an optimum timing set in advance in response to the acoustic lens 65. The reflected wave signal c will produce a reflected signal from the sample 67 at a time when the first and second reflected waves produced by the multiplex reflection within the acoustic lens 65 are avoided. The timing tl for producing the first and second reflected waves within the lens is given by $tl=2L/C_1$ where L is the lens length and $C_1$ is the sound velocity within the lens. The timing $t_s$ at which the reflected wave from the sample is produced is given by $t_s=2L/C_1+2f/C_2$ where f is the focal distance of the lens and $C_2$ is the sound velocity in water in case water is used for the ultrasonic wave transmitting medium 66. Therefore, the timing tg of the gate signal d is so set that the width of the sample reflected wave may be covered by the time width T of the gate signal d. That is to say, by only changing the change switch 61B in response to the acoustic lens 65 to be used, the gate signal d of the required time width T having the desired timing tg is fed to the gate 68A. From this fact, as shown in FIGS. 8 and 9, the gate timing will be able to be selected by changing the change switch 61B when the timing $t_{g1}$ and $t_{g2}$ of the gate signal d are set in advance in the timing controller 61A in response to the reflected waves from the sample in using the respective lenses so that two acoustic lenses in which the timings for producing the first and second reflected waves within the lens are respectively $tl_1$ and $tl_2$ may be used as replaced. Needless to say, a plurality of gate timings can be selected not only for the two acoustic lenses but also for a plurality of acoustic lenses.

Figure 10:
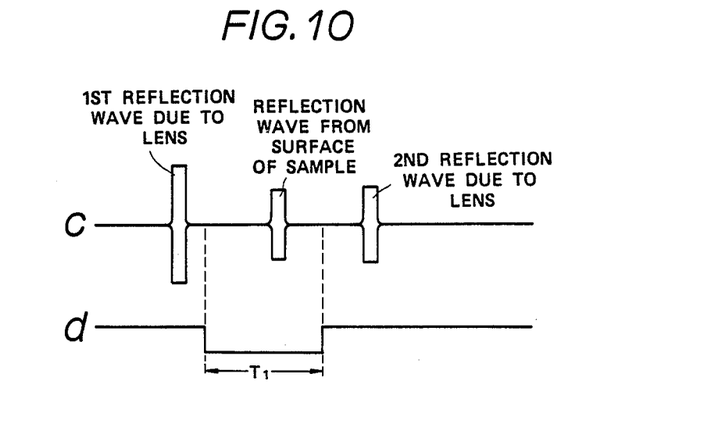
FIGS. 10 and 11 are waveform views for explaining the fourth embodiment of the present invention.
Figure 11:
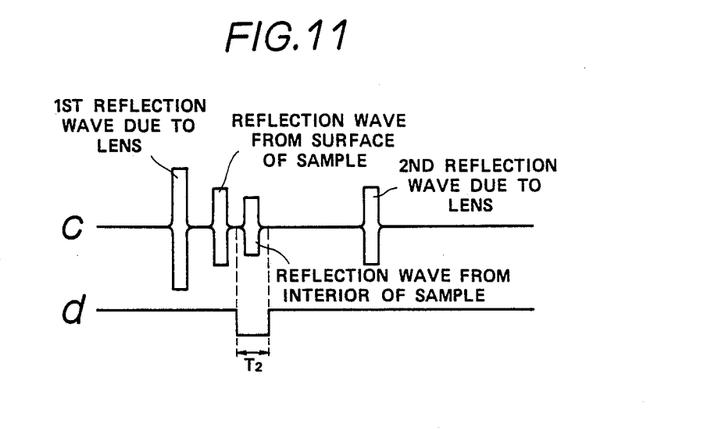

By the way, in the above mentioned embodiment, gate timings can be selected in response to a plurality of acoustic lenses. However, in the present invention, by making the gate position (gate time width) variable for one acoustic lens, the reflected wave from the sample surface can be removed and only the signal from the interior of the sample can be taken out to be observed. For example, the information from the sample surface will be able to be obtained when the time width of the gate signal d is set so as to be $T_1$ as shown in FIG. 10 when the acoustic lens 65 is focused on the surface of the sample 67 and then the information from the interior of the sample will be able to be obtained when the time width of the gate signal d is set so as to be $T_2$ as shown in FIG. 11 when the acoustic lens 65 is focused in the interior of the sample 67.

According to this embodiment, there is no complicated adjustment accompanying the replacement of an acoustic lens, that is, an ultrasonic head, the head can be quickly replaced and adjusted to make the best observation and the information within the sample can be clearly observed.

By the way, it is apparent that working modes different in a wide range can be formed without deviating from the spirit and scope of the present invention. The present invention is not restricted by any specific working mode except being limited to the appended claims.

What is claimed is:

1. An ultrasonic microscope for examination of a sample, said microscope having an acoustic lens assembly, and having a structure to emit acoustic waves from a specific frequency pulse transmitter to a spherical lens part through a propagation medium and to receive a reflected sample signal and to produce a sample image on a cathode-ray tube by scanning said acoustic lens in a raster pattern, said ultrasonic microscope comprising:
   a plurality of acoustic lenses forming said acoustic lens assembly, which lenses are selectably interchangeable with one another for a specific purpose;
   a plurality of frequency units provided for respective frequencies, and having transmitted pulse generators and receivers;
   a plurality of matching means corresponding to said respective frequencies; and
   a changing switch means to generate a change signal for changing a corresponding frequency unit and matching means to be operable with a selected acoustic lens in response to the selection of said selected acoustic lens.

2. An ultrasonic microscope according to claim 1, further comprising:
   a discriminating code means for outputting a discriminating code corresponding to said selected acoustic lens;
   a change controlling means for controlling said changing switch means to change said corresponding frequency unit and said matching means to be operable with said selected acoustic lens in response to said code and to generate a pair of corresponding signals.

3. An ultrasonic microscope according to claim 2 wherein said discriminating code includes the frequency, operating distance and opening angle of the acoustic lens.

4. An ultrasonic microscope according to claim 3 wherein said change controlling means outputs the signal of the frequency to be used, operating distance and opening angle of the acoustic lens to be replaced.

5. An ultrasonic microscope according to claim 4 wherein said change signal can be manually set.

6. An ultrasonic microscope for examination of a sample, said microscope having an acoustic lens assembly, and having a structure to emit acoustic waves from a specific frequency pulse transmitter to a spherical lens part through a propagation medium and to receive a reflected sample signal and to produce a sample image on a cathode-ray tube by scanning said acoustic lens in a raster pattern, said ultrasonic microscope comprising:
   a plurality of acoustic lenses forming said acoustic lens assembly, which lenses are selectably interchangeable with one another for a specific purpose;
   a plurality of frequency units provided for respective frequencies, and having transmitted pulse generators and receivers;

a plurality of matching means corresponding to said respective frequencies;

a gate timing generating means for generating gate signals at a plurality of different timings in response to the lens length of said acoustic lens to make it possible to receive the reflected acoustic wave returning from the sample; and a timing controlling means for outputting control signals to determine the timing of the gate signal by the selection of an acoustic lens on said gate timing generating means.

7. An ultrasonic microscope according to claim 6 wherein said gate timing generating means is variably changed from a timing representing an acoustic lens of a specific lens length in order to receive the reflected acoustic wave from the sample surface to a timing which enables the acoustic lens to receive the reflected acoustic wave from the interior of the sample.

* * * * *